United States Patent
Dallas et al.

[11] Patent Number: 5,976,467
[45] Date of Patent: Nov. 2, 1999

[54] AIRBORNE CONTAMINANT INDICATOR

[75] Inventors: Andrew J. Dallas, Apple Valley; Kristine Marie Graham, Minnetonka; Timothy H. Grafe, Edina, all of Minn.

[73] Assignee: Donaldson Company, Inc., Minneapolis, Minn.

[21] Appl. No.: 08/893,876

[22] Filed: Jul. 11, 1997

[51] Int. Cl.[6] .................................................. G01N 30/48
[52] U.S. Cl. ................................ 422/86; 422/83; 422/88; 436/38; 436/61; 436/100; 436/113; 436/167; 436/169; 436/181
[58] Field of Search .................................. 422/59, 60, 83, 422/86, 88; 436/38, 61, 100, 111–113, 163, 167, 169, 170, 181

[56] References Cited

U.S. PATENT DOCUMENTS

| | | | |
|---|---|---|---|
| 3,025,142 | 3/1962 | Williams | 422/60 X |
| 3,350,175 | 10/1967 | McConnaughey et al. | 436/113 X |
| 3,512,939 | 5/1970 | Hugi . | |
| 3,528,780 | 9/1970 | Radawski | 436/113 |
| 4,259,287 | 3/1981 | Leichnitz | 422/60 X |
| 4,459,266 | 7/1984 | Lamoreaux | 422/86 |
| 4,471,186 | 9/1984 | Yoshioka | 422/86 X |
| 4,530,706 | 7/1985 | Jones . | |
| 4,692,309 | 9/1987 | Pannwitz . | |
| 4,875,914 | 10/1989 | Wireman | 96/136 |
| 5,069,879 | 12/1991 | Leichnitz et al. | 422/86 |
| 5,120,511 | 6/1992 | Luft | 422/86 |
| 5,173,263 | 12/1992 | Lee | 422/88 |
| 5,290,345 | 3/1994 | Osendorf et al. | 96/129 |

FOREIGN PATENT DOCUMENTS

| | | | |
|---|---|---|---|
| 1 157 355 | 11/1983 | Canada . | |
| 62-19765 | 1/1987 | Japan | 436/181 |

OTHER PUBLICATIONS

M. Yanagawa et al. *J. Japan Soc. Air Pollut.* 1989, 24, 290–297.
C.K. Boo et al. *Chem. Abstr.* 1971, 75, 101001e.
A.L. Linch "Evaluation of Ambient Air Quality by Personnel Monitoring" CRC Press Inc: Cleveland, Ohio, 1974, pp. 40–42,45, & 178–180.
K. Leichnitz "Detector Tube Handbook" Dräger, 1979 4th ed. pp. 11,12,18,35,37,84,153,195,197,198,201 & 202.
D. Callahan et al. *Talanta* 1993, 40, 431–444.
Abstract of SU 1605191.

*Primary Examiner*—Arlen Soderquist
*Attorney, Agent, or Firm*—Merchant & Gould P.C.

[57] ABSTRACT

An indicator system provides a visual indication of the cumulative level of an airborne contaminant. An indicator has a transparent sheath with support medium treated with acid and a pH indicator, as the contaminant is adsorbed, the color changes along the medium. The indicator system may be used with an adsorptive filter system to predict the life of adsorption bed assemblies. A sample flow is taken upstream of the adsorption beds and is calibrated with a flow meter and valve. By monitoring the indicator, an accurate prediction of adsorption bed life may be made.

13 Claims, 4 Drawing Sheets

AIRBORNE CONTAMINANT INDICATOR

BACKGROUND

1. Field of the Invention

The present invention generally relates to a method and apparatus for indicating the presence of airborne contaminants and accumulation of airborne contaminants, such as organic and inorganic bases, and more particularly to predicting the life of filter systems for removing the airborne contaminants.

2. Prior Art

Gas adsorption beds are used in many industries to remove airborne contaminants, such as organic bases, to protect people, the environment and often, a critical manufacturing process for the products which are manufactured. A specific example of an application for gas adsorption beds is the semiconductor industry where products are manufactured in an ultra-clean environment, commonly known in the industry as a "clean room". The manufacturing process typically requires the use of substances such as solvents to be used in the clean room environment. The use of these substances presents a problem when vapors are formed during the process which may contaminate the air and other processes in the room if they are not properly removed. In addition, many environments have several gases that may naturally occur in the ambient air that may contaminate the products and/or processes and are not removed by normal particulate filters. Typical contaminants that are produced by such processes are airborne bases, such as ammonia, organic amines and N-Methyl-2-pyrrolidone.

To eliminate the problem, contaminated air is often drawn through a granular adsorption bed assembly having a frame and adsorption medium, such as activated carbon retained within the frame. The adsorption medium adsorbs the gaseous contaminants from the air flow and allows clean air to be returned to the clean room and/or process. It can be appreciated that the removal efficiency of such beds is critical in order to protect the processes and the products that are involved.

It can further be appreciated that since the removal process involves passage of air through an activated carbon bed that adsorbs or chemically reacts with the airborne contaminants, there is no measurable pressure change as occurs when particulate filters are loaded. Therefore, it is difficult to directly monitor the status and deterioration of the activated carbon bed. Monitors placed downstream may detect performance, efficiency, or when a failure has occurred and that the adsorption beds are spent. However, presently available sensors may not be sensitive enough to work at the contaminant threshold levels which are critical in the semiconductor industry and are often quite costly. A problem with sensors having acceptable sensitivity is that they are often specific to a single contaminant. Although such sensors may detect a low level of one contaminant, others may accumulate to high levels and remain undetected. However, once there is an indication that an adsorption bed is spent, it is often too late and the process or products have often been ruined or damaged.

Other systems have been devised which can monitor adsorption bed life such as placing the beds in series. When adsorption beds are placed in series, a sensor may be placed in series intermediate the two adsorption beds. Therefore, as one adsorption bed becomes spent and the sensor indicates the presence of a contaminant, the second adsorption bed is still effective and failures are prevented. However, such detection systems have several drawbacks. When two adsorption beds are used, the pressure drop is doubled. This may be critical in some applications. In addition, once the first bed has been indicated as being spent, the adsorption beds are normally rotated in a sometimes complicated manner. Such rotation increases the maintenance and down time of such a system. At other times, both adsorption beds may be changed out, thereby decreasing labor, but also shortening the useful life of the downstream adsorption beds as they are removed prior to being fully spent.

Other systems utilize a sensor placed directly in the adsorption bed. However, in very thin adsorption beds, such a sensor may take up valuable space. In addition, an interface for detecting the presence of contaminants within an adsorption bed requires seals and can be complicated and expensive.

It can be appreciated that if the filtered air can be distributed in a balanced, even manner over the adsorption beds, a reliable prediction of the expected useful duration of each bed would enable a longer change out interval period without failure. It can be appreciated that achieving the greatest possible change out interval without failure would decrease filter materials cost and labor costs utilized in changing the adsorption bed filters.

It is desirable to have an indication of the actual amount of contaminant that the filter beds have been exposed to based on a known filter capacity and being able to accurately predict an optimal change out period for the adsorption beds. Such a process is more precise if the actual flow passing through the filters is known and the prediction based on a flow which is proportional to the actual flow through the adsorption beds. By sampling upstream of the adsorption beds, an accurate prediction of the contaminants which are flowing to the adsorption beds can be made.

It can be seen then that an indicator system is needed that detects the cumulative levels of airborne contaminants. Such a system should be able to sample a proportional amount of airborne contaminants that are flowing past an adsorption bed device. Such an indication system should provide a clear visual indication of the bed usage and indicate when the adsorption beds should be changed. In addition, as contaminant concentrations may vary, the system should provide a real time indication of cumulative contamination levels for predicting the change out interval based on the actual contaminant flow past the adsorption bed. It can also be appreciated that such a system should provide for a variable safety factor to ensure that adsorption bed failures do not occur. Such a system should also be able to measure the presence and cumulative level of such contaminants in an environment and provide a visual indication. The present invention addresses these as well as other problems associated with indicating the presence of airborne contaminants.

SUMMARY OF THE INVENTION

The present invention is directed to a system and method for indicating the presence of airborne bases. Such a system may be used in clean rooms and other applications wherein air quality is critical.

The indicator system includes a valving arrangement to control flow into and out of the system. A probe is utilized to obtain a sample of air. In one embodiment, a sample taken is proportional to the actual flow rate from the air being sampled. Therefore, the system can be used as a predictor with greater accuracy as contamination levels vary.

The system uses a flow meter to monitor and calibrate the system. An indicator device includes a sheath, such as a tube, having an indicating medium therein. As contaminants encounter the tube from a first end, the specially treated medium will change colors to indicate the presence of contaminant. As the tube is substantially transparent, an advancing front of color changing affected medium within the sheath is visually detectable. Therefore, as additional contaminant passes through the medium, a greater amount is affected and changes color to indicate the increasing levels. Flow is maintained in a proportional rate to actual flow by a calibrated flow meter. An ejector type pump which is actuated by compressed air maintains flow through the system.

As typical clean room processes emit ammonia, amines and other bases, the medium is typically a silica gel treated with an acid, such as sulfuric acid. The mixture is treated with an indicator, such as bromophenol blue, which changes color from yellow to blue upon an increase in pH from exposure to a base. Therefore as the airborne bases are passed through the medium, a front of spent medium of a different color advances along the tube.

Adsorption type beds which are commonly used in clean room settings do not clog as normal filters do and are difficult to monitor for determining their change interval. Although sensors may be utilized downstream of the filters to detect when the adsorption beds are spent, such devices are expensive and often do not have sufficient sensitivity to monitor the low levels of airborne contaminants. In addition, the critical nature of the processes is such that by the time the expiration of the adsorption beds is detected, damage may have already been done and it is too late. Therefore, it is advantageous to predict when the adsorption beds will have scheduled maintenance or need changing and to have a maximum interval which provides for changing of the filters prior to any failure.

To predict an interval, a probe for the system is placed upstream of the filters to sample the same air flow which is passing over the adsorption beds. In this manner, by knowing the rate of the advancing front along the tube and the flow rate over the adsorption beds and their deterioration rate, a monitoring system can be utilized to predict when the adsorption bed interval expires. However, as proportional flow is maintained, color in the advancing front along the indicator medium also changes color at a rate proportional to the change of the actual adsorption bed.

These features of novelty and various other advantages which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT

Figure 1:
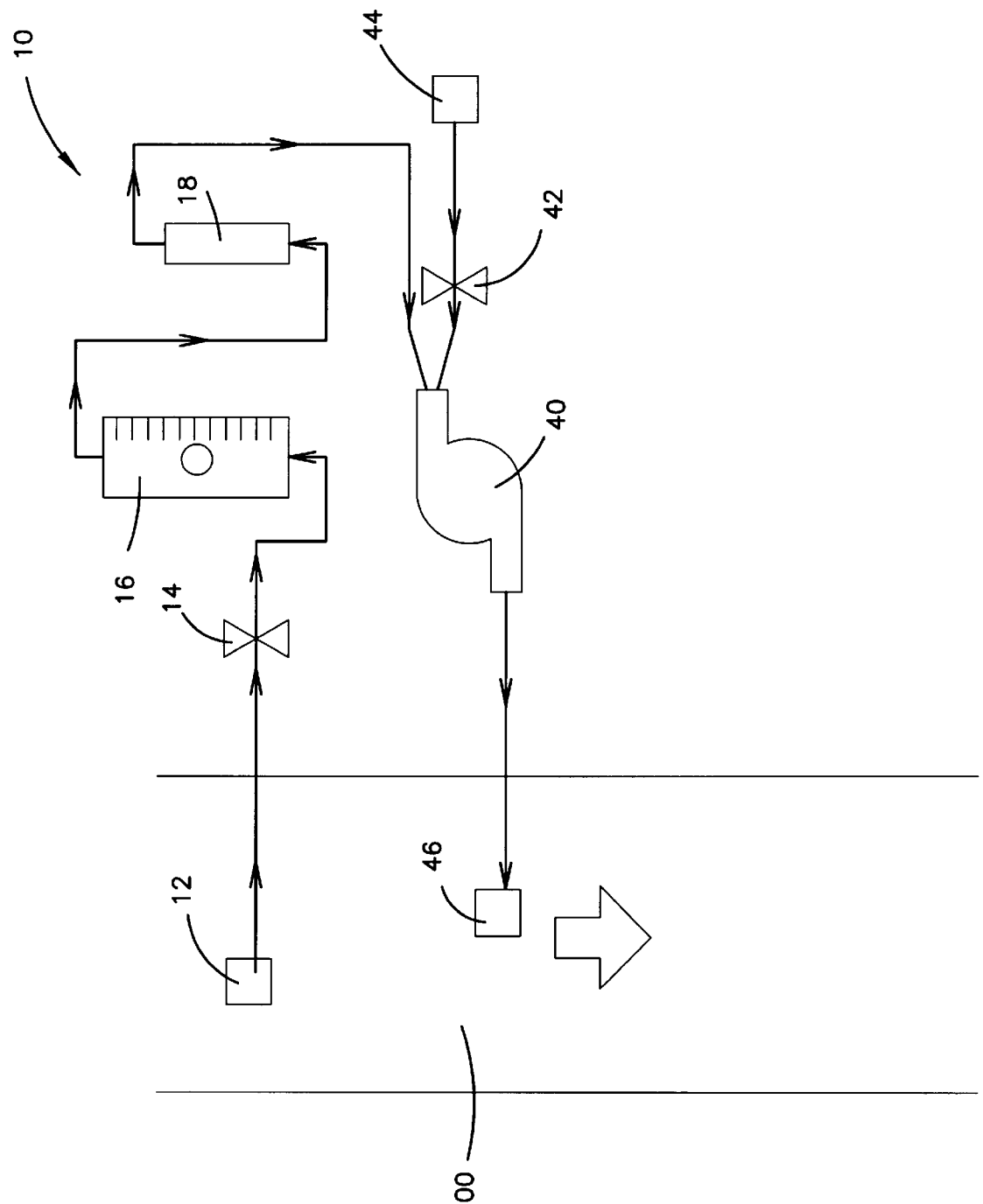
FIG. 1 shows a diagrammatic view of an indicator system according to the principles of the present invention.

Referring now to the drawings, and in particular FIG. 1, there is shown a system, generally designated 10, for indicating the presence and level of an airborne contaminant. The system includes a probe 12 for sampling air from a duct or ambient air volume 100. The indicator system 10 also includes a flow meter 16 with a control valve between the probe 12 and the flow meter 16. An indicator 18 is downstream of the flow meter 16. A pump 40 maintains flow through the indicator system 10. In a preferred embodiment, the pump is an ejector type pump such as Model No. #-79700-00, available from Cole-Parmer Company, which is actuated by a compressed air supply 44. A valve 42 acts as a safety valve between the compressed air supply 44 and the pump 40. The valve 14 controls flow to the system 10 and is calibrated by flow meter 16. In a preferred embodiment, the flow is proportional to the sampled flow. The pump 44 returns the sample air through a vent 46 to a duct and back to the sampled or ambient air 100. It can be appreciated that for some monitoring applications, such as sampling ambient air or flows, the pump 40, flow meter 16 and valve 14 may not be used.

Figure 2:
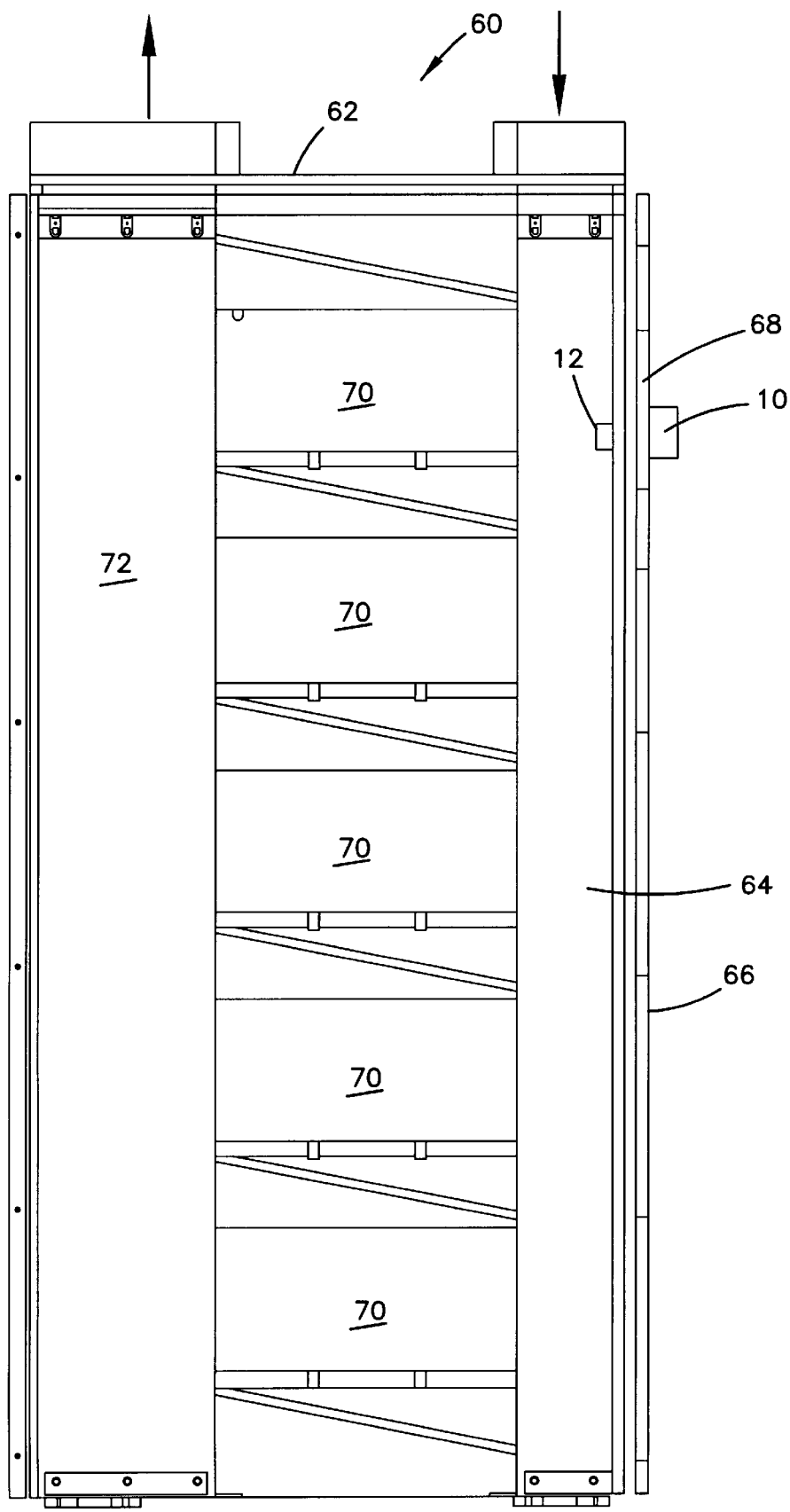
FIG. 2 shows a side elevational view of a counterflow adsorption bed apparatus having the indicator system shown in FIG. 1.

Referring now to FIG. 2, the indicator system 10 may be used with an adsorption filtering system 60. Such a filtering system 60 typically includes a housing 62 with an access door 66. The interior of the housing has an inlet plenum 64 extending vertically past a stack of adsorption beds 70. Flow passes from the inlet plenum 64 in parallel through the adsorption beds 70 to an outlet plenum 72. The treated air is circulated back to the ambient air. Another system is also shown in U.S. Pat. No. 5,290,345 to Osendorf and assigned to Donaldson Company, assignee of the present invention.

In the configuration shown in FIG. 2, the probe 12 is placed at the inlet plenum prior to being treated through the adsorption beds 70. However, such systems may be used to measure contaminant levels in the ambient air or at different locations in a filter system, such as downstream of the adsorption beds 70. In the configuration shown, the indicator system 10 can be used as a predictor of adsorption bed life. It can be appreciated that the adsorption beds 70 are positioned to receive a balanced air supply through the beds so that the deterioration rate of each adsorption bed 70 is equal. The indicator system 10 is used as a predictor of adsorption bed life and changeover interval, rather than as an indicator of when failure has already occurred, as in the prior art sensors. As explained hereinafter, the indicator 18 also gives an indication of the deterioration level of the adsorption beds 70.

Figure 3:
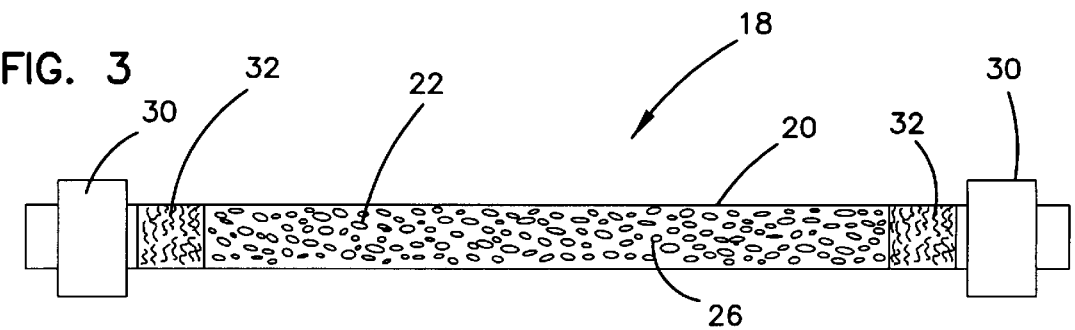
FIG. 3 shows a side elevational view of an indicator device for the system shown in FIG. 1.
Figure 4:
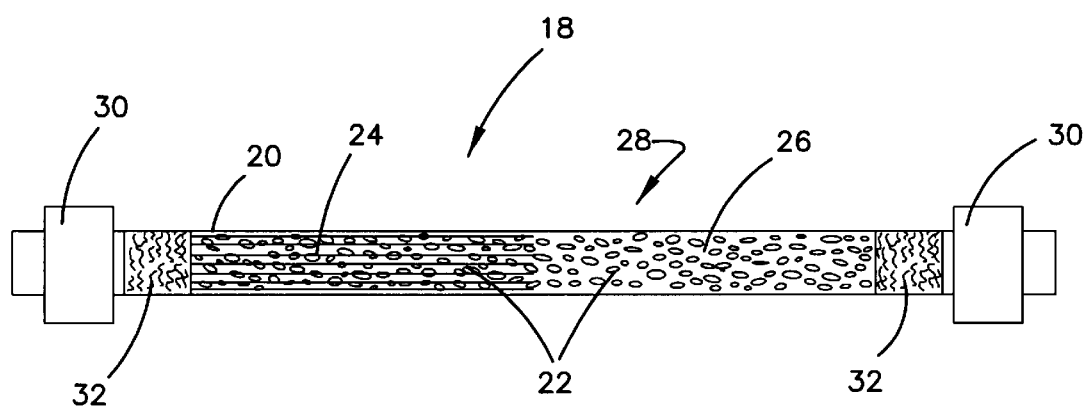
FIG. 4 shows a side elevational view of the indicator device shown in FIG. 2 with a portion of the indicator medium changed.
Figure 5:
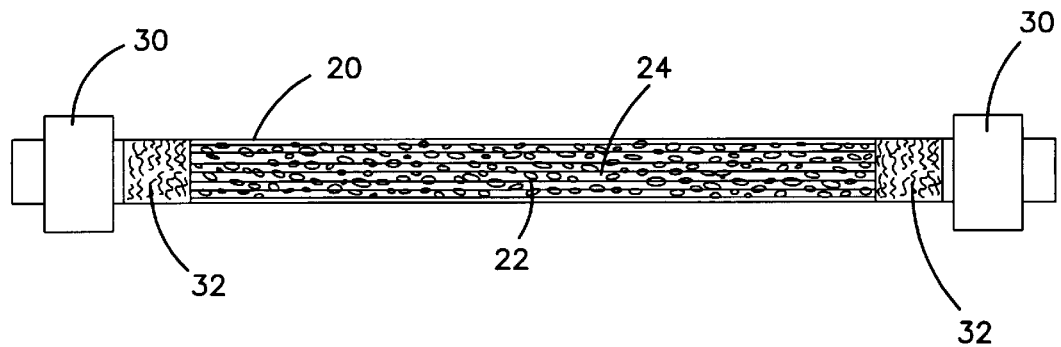
FIG. 5 shows a side elevational view of the indicator device shown in FIG. 2 with the indicator medium shown fully changed; and, FIG. 6 shows a flow chart of a method of calibrating an indication system for predicting the interval of an adsorption device according to the principles of the present invention.

Referring now to FIGS. 3–5, there is shown greater detail of the indicator 18. The indicator 18 includes a tube 20 which preferably has a transparency level sufficient to see a colormetric indicating medium 22 within the tube. In the preferred embodiment, the tube 20 is quite narrow, on the order of an ⅛ inch outside diameter, an inside diameter of 0.08 inches, and made from a suitable material such as Teflon ™. At each end of the tube 20 are porous plug elements 32 such as glass wool, which maintain the indicating medium 22 within the tube 20 tightly packed. The tube 20 also includes fittings 30 such as Swagelok™ elements or other suitable fittings for connecting to mating fittings giving an overall length of about 7.5 inches. The fittings 30 provide for easy removal and replacement of the indicator 18 when the indicating medium 22 is spent or when associated adsorption beds are changed and it is desired to have a fresh indicator 18 associated with the fresh adsorption bed assemblies 70. The medium 20 is typically a coated or impregnated silica gel which is designed with advancement rate which coincides with the life of the filter bed system 70. Examples of other suitable medium include glass beads, porous polymers and alumina. It can be appreciated that by calibrating the flow rate, tube size, silica gel, mesh size and surface area, the amount of acid, and/or the flow rate, it is possible to predict an optimum interval for changing a filter bed assembly 70 by monitoring the amount of spent indicator medium 24.

In one embodiment, the indicating medium 22 is typically a coated or impregnated silica gel. A specific mesh and surface area of the silica gel must be chosen for the specific needs of each indicator system 10. It can be appreciated that a smaller particle size will provide for a sharper divide in the color change of the advancing front of affected medium 24, but will result in a higher pressure drop for the sampled air. An example of a typical medium for airborne bases is a 100/200 mesh silica gel or beads which has a specific surface area of approximately 500 square meters per gram. To prepare the gel, it is first immersed in a sulfuric acid solution for approximately two hours after which the excess acid is poured off and the silica gel is washed with distilled water several times. The final solution of the silica gel is filtered and dried. Dried samples are wetted with an aqueous solution of isopropanol, to which is added a known amount of an appropriate indicator. An example of an indicator that has a color change at an appropriate pH is bromophenol blue. However, it can be appreciated that depending on the needs of the system and the type of contaminants that are being removed, other indicator mediums such as phenolphthalein, thymolphtalein phenol red, and other colormetric indicators changing at a different pH may be utilized. In addition, it can be appreciated that the concentration of the indicator that is used depends on the intensity of the color that is desired. It has been found that a 0.5% by weight bromophenol blue concentration works well. It can also be appreciated that other types of acid such as hydrochloric acid or acetic acid may be used depending on the pH range which is desired and the indicator being used. A solution of the acidified silica gel, the water/isopropanol mixture and the bromophenol blue indicating substance is stirred for several minutes. After the solution is allowed to stand, it is washed with isopropanol. The resulting gel is dried in an oven at approximately sixty degrees (60°) Celsius. The resulting silica gel is a bright yellow but upon exposure to a base, such as ammonia, the color changes from yellow to blue. Higher concentrations of the bromophenol blue yield an orange silica gel which changes to a blue/purple color upon exposure to a base. The indicating medium 22 is vacuum packed into the tube 20 and retained by the plugs of glass wool 32.

Once a tube is prepared, it can be calibrated by exposing it to a controlled air flow which contains a known amount of the contaminant or airborne base. With the flow meter 16, an amount of sample air passing through the system may be measured. The advancing color front 28 between spent medium 24 and fresh medium 26, as shown in FIG. 4, is measured as a function of the amount of contaminant if the resulting curve is achieved showing the deterioration rate and color change through the indicating medium 22. This curve can be compared to the known capacity of the adsorption bed 70 and the expected breakthrough time of the adsorption bed 70 can be predicted. The flow rate through the indicating system 10 can be increased or decreased using the flow meter 16 and the valve 14 depending on the safety factor required.

Referring to FIGS. 3–5, it can be appreciated that when the indicator 18 is fresh, the indicating medium 22 shows an unchanged medium 26 of the initial color, typically yellow. However, as shown in FIG. 4, as more contaminant passes through the indicator 18, the medium changes color and the spent medium 24 can be visually detected through the tube 20. A front 28 provides a clearly visually perceptible line advancing along the tube 20. As shown in FIG. 5, when the medium 22 is substantially entirely affected, all of the medium 22 changes color to show the spent medium 24, indicating that the adsorption bed filter 70 should be changed.

It can be appreciated that the above example is for a system for removing airborne bases such as ammonia. However, it can be appreciated that other substances may be utilized for measuring the presence of other types of airborne compounds and used just as effectively. In addition, although the above described example provides for predicting the life of an adsorption bed assembly, the indicator system may be used to measure the presence of a contaminant and the cumulative concentration of such a contaminant over time and in ambient conditions that do not have a flow or an adsorption device.

Figure 6:
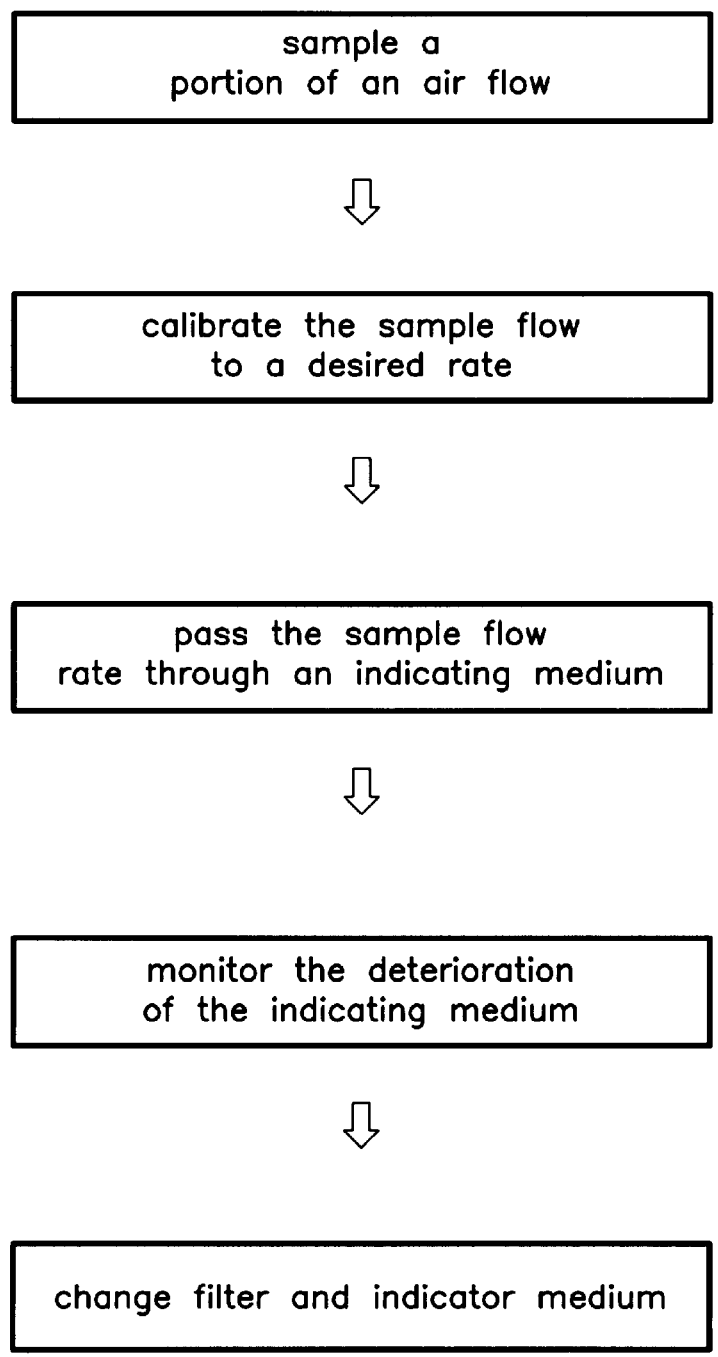

Referring now to FIG. 6, there is shown a method for predicting the life of an adsorption filter using the indicator system 10 shown in FIG. 1. When new adsorption medium, such as for example, activated carbon, in an adsorption bed 70 is installed, a fresh indicator 18 having fresh medium 24 is also installed. Utilizing the flow meter 16 and the control valve 14, the sampled flow is calibrated during installation to provide a sufficient flow so that the proper rate of change indicated by the indicator system 10 matches the life of the adsorption bed 70 with the desired safety factor. After initial installation, further calibration is not necessary unless flow through the adsorption beds 70 changes. However, monitoring of the flow to ensure that the system is working properly can still be utilized with the flow meter 16. If the flow has been properly calibrated, during operation, flow is directed through the probe 12 and the indicator 18. The flow meter 16 and valve 14 ensures that proper flow is maintained that is proportional to the flow being monitored. As the indicator tube is exposed to a greater amount of contaminants over time, the front 28 of spent medium 24 moves along the length of the indicator 18 as shown in FIGS. 3–5. This provides a visually perceptible indication which can be monitored. As the rate of the front 28 in the tube is comparable to the deterioration rate of the adsorption bed 70, it can be appreciated that the usage and life of the adsorption beds 70 can be predicted by viewing the indicator 18. When the indicator 18 indicates that the indicator medium 22 is substantially spent by a total change in color, as shown in FIG. 5, system operators can observe that it is time to change the adsorption beds 70.

Replacement of the tube 18 is preferably performed at the same time as the beds for adsorption bed media 70 are changed. If the flow within the indicator system 10 has already been calibrated to the flow of the adsorption filtering system, it is not necessary to recalibrate, so that the indicator tube 18 is the only element replaced at the same time as the adsorption beds 70. A new indicator tube 18 serves to predict the rate of usage of the replacement adsorption bed 70.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An indicator system for indicating the level of an airborne contaminant in an adsorption bed, the system comprising:

an adsorption bed for removal of airborne contaminant from a main airflow, an indicator comprising a tube having a substantially transparent portion, wherein the tube is filled with coated medium having a color-changing dye;

a pump for supplying a sample airflow from the main airflow, the sample airflow passing through the indicator;

a flow meter for measuring and calibrating the sample airflow relative to the main airflow through the adsorption bed;

wherein the sample airflow passes from the pump through the flow meter and passes from a first end to a second end of the tube such that the color-changing dye defines a visible changing color front along the tube as the dye is exposed to the airborne contaminant, the indicator providing a real time indication of increasing cumulative exposure of the adsorption bed to the airborne contaminant.

2. An indicator system according to claim 1, wherein the color changing dye comprises a pH indicator.

3. An indicator system according to claim 1, wherein the coated medium is mixed with an acid solution.

4. An indicator system according to claim 1, further comprising a control valve controlling the sample airflow.

5. An indicator system according to claim 4, wherein the control valve is calibrated to sample at a predetermined rate.

6. An indicator system according to claim 1, wherein the coated medium comprises a silica gel.

7. An indicator system according to claim 1, wherein the coated medium comprises glass beads.

8. A method of indicating a deterioration level of an adsorptive medium for removing airborne contaminants and having a first flow passing from upstream to downstream through the adsorptive medium, comprising the steps of:

obtaining a sample airflow proportional to the first flow upstream of the adsorptive medium;

passing the proportional air sample through indicating medium having a color sensitive coating, the color sensitive coating changing color as a moving front in response to exposure to the airborne contaminants;

calibrating the proportional air sample so that the moving front in the indicating medium corresponds to the deterioration level of the adsorptive medium.

9. A method according to claim 8, wherein the proportional air sample passes through the indicating medium from a first side to a second side of a transparent sheath retaining the indicating medium.

10. A method according to claim 9, comprising the further step of calibrating the sample flow through the indicating medium so that the medium changes completely before the adsorption medium requires replacement.

11. A method according to claim 9, comprising the further step of calibrating the sample flow through the indicating medium so that medium changes completely when the adsorption medium requires replacement.

12. A measuring system for measuring the life of an adsorptive filter for removing an airborne contaminant, the adsorptive filter having flow passing from upstream to downstream through the filter, the system comprising:

an adsorptive filter having a flow therethrough;

an indicator comprising:

a substantially transparent sheath having an inlet for sampling air upstream of the adsorptive filter at a rate proportional to the flow through the adsorptive filter; and a visual indicator within the sheath adapted for receiving the air sample flow, the visual indicator indicating the presence of the airborne contaminant in the air sample flow, the rate of air sample flow being calibrated relative to a deterioration rate of the adsorptive filter.

13. A measuring system to claim 12, further comprising a control valve for varying the sample flow rate.

* * * * *